(12) United States Patent
Brennen

(10) Patent No.: US 7,282,705 B2
(45) Date of Patent: Oct. 16, 2007

(54) MICRODEVICE HAVING AN ANNULAR LINING FOR PRODUCING AN ELECTROSPRAY EMITTER

(75) Inventor: Reid A. Brennen, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 737 days.

(21) Appl. No.: 10/741,901

(22) Filed: Dec. 19, 2003

(65) Prior Publication Data

US 2005/0133713 A1 Jun. 23, 2005

(51) Int. Cl.
*H01J 49/04* (2006.01)
*F15C 1/06* (2006.01)

(52) U.S. Cl. ............ 250/288; 137/833; 137/827; 210/243; 210/656; 210/748; 204/600; 204/601; 239/690; 422/68.1

(58) Field of Classification Search ........... 250/288; 137/833, 827; 210/243, 656, 748; 204/600, 204/601; 239/690; 422/68.1; 436/173
See application file for complete search history.

(56) References Cited

U.S. PATENT DOCUMENTS

| | | | |
|---|---|---|---|
| 5,291,226 A | 3/1994 | Schantz et al. | |
| 5,305,015 A | 4/1994 | Schantz et al. | |
| 5,500,071 A | 3/1996 | Kaltenbach et al. | |
| 5,571,410 A | 11/1996 | Swedberg et al. | |
| 5,645,702 A | 7/1997 | Witt et al. | |
| 5,660,680 A | 8/1997 | Keller | |
| 5,792,943 A | 8/1998 | Craig | |
| 5,872,010 A | 2/1999 | Karger et al. | |
| 5,969,353 A | 10/1999 | Hsieh | |
| 6,459,080 B1 | 10/2002 | Yin et al. | |
| 6,517,736 B1 | 2/2003 | Flannery et al. | |
| 6,803,568 B2 * | 10/2004 | Bousse et al. | 250/288 |
| 7,213,339 B2 | 5/2007 | Ohman et al. | |

FOREIGN PATENT DOCUMENTS

| | | |
|---|---|---|
| DE | 10154601 A1 | 6/2002 |
| DE | 10153663 A1 | 7/2002 |
| EP | 0964428 A3 | 8/2002 |

(Continued)

OTHER PUBLICATIONS

U.S. Appl. No. 09/711,804, filed Nov. 13, 2000, Brennen et al.

(Continued)

*Primary Examiner*—Jack I. Berman

(57) ABSTRACT

A microdevice is constructed from a substrate having a microchannel formed therein and a cover plate arranged over the substrate. The cover plate in combination with the microchannel at least partially defines a conduit within the microdevice. The conduit has a surface that extends from an upstream region toward a downstream region and terminates at an opening. The microdevice also includes an annular lining that conforms to the conduit surface at the downstream region and extends from the opening toward the upstream region in the conduit. An emitter may be produced in situ by depositing an emitter material on the annular lining. In addition, material may be removed from the cover plate and/or substrate about the opening. As a result, an exterior microdevice surface is formed and a downstream portion of the emitter is exposed that protrudes from the exterior surface.

32 Claims, 6 Drawing Sheets

FOREIGN PATENT DOCUMENTS

| | | |
|---|---|---|
| WO | WO98/35376 | 8/1998 |
| WO | WO 00/22409 | 4/2000 |

OTHER PUBLICATIONS

Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35-36.

Ehrfeld et al. (1988), "LIGA Process: Sensor Construction Techniques via X-Ray Lithography," *Technical Digest, IEEE Solid-State Sensor and Actuator Workshop*, pp. 1-4, Hilton Head, SC.

Figeys et al. (1997), "A Microfabricated Device for Rapid Protein Identification By Microelectrospray Ion Trap Mass Spectrometry," *Anal. Chem.* 69(16):3153-3160.

Guckel et al. (1991), "Fabrication and Testing of the Planar Magnetic Micromotor," *J. Micromech. Microeng.* 1:135-138.

Li et al. (2000), "Separation and Identification of Peptides From Gel-Isolated Membrane Proteins Using a Microfabricated Device for Combined Capillary Electrophoresis/Nanoelectrospray Mass Spectrometry," *Anal. Chem.* 72(3):599-609.

Licklider et al. (2000), "A Micromachined Chip Based Electrospray Source for Mass Spectrometry," *Anal. Chem.* 72(2):367-375.

Ramsey et al. (1997), "Generating Electrospray From Microchip Devices Using Electroosmotic Pumping," *Anal. Chem.* 69(6)::1174-1178.

Schultz et al. (1999), "A Fully Integrated Monolithic Microchip-Based Electrospray Device for Microfluidic Separations," *47th ASMS Conference on Mass Spectrometry and Allied Topics* (Jun. 13-17).

Zhang et al. (1999), "Microfabricated Devices for Capillary Electrophoresis-Electrospray Mass Spectrometry," *Anal. Chem.* 71(15):3258-3264.

Zhang et al. (2000), "A Microdevice with Integrated Liquid Junction fore Facile Peptide and Protein Analysis by Capillary Electrophoresis/Electrospray Mass Spectrometry," *Anal. Chem.* 72(5):1015-1022.

Znotins et al. (1987), "Excimer Lasers: An Emerging Technology in Materials Processing," *Laser Focus/Electro-Optics*, pp. 54-70.

European Search Report for Application No. EP 04 25 7232, dated Sep. 5, 2005, by Examiner M. Meister in Berlin on Aug. 24, 2005.

\* cited by examiner

MICRODEVICE HAVING AN ANNULAR LINING FOR PRODUCING AN ELECTROSPRAY EMITTER

TECHNICAL FIELD

The present invention generally relates to microdevices having electrospray emitters and to the production of such emitters. More specifically, the invention relates to the use of an annular lining that conforms to a downstream surface of a microdevice conduit to produce an electrospray emitter protruding from an exterior surface of the microdevice.

BACKGROUND

Electrospray ionization (ESI) technology allows ions to be produced from a liquid solution and introduced into an analytical device such as a mass spectrometer. Typically, an aerosol is produced in a spray chamber of the analytical device by passing a fluid sample through a capillary such that the capillary serves as an electrospray emitter and has a terminus subjected to an electric field within the chamber. The electric field is usually generated by placing a source of electrical potential, e.g., an electrode or sample introduction orifice, near the capillary terminus, wherein the source is held at a voltage potential difference with respect to the capillary terminus. As a result, a large electric potential gradient is created at the terminus of the electrospray emitter.

The emitter may be operated in a positive or negative ion mode by creating a negative or positive potential gradient, respectively. In the positive-ion mode of operation, a high positive voltage is applied to the electrospray emitter and/or a high negative voltage at the electrode or sample introduction orifice. In such case, the imposed field will penetrate the liquid at the capillary tip and the accumulated positive charge at the surface leads to destabilization of the surface to form a cone (Taylor cone), because the positive ions are drawn down but cannot escape from the liquid. At a sufficient high field, bulk liquid from the Taylor cone may be broken into charged liquid droplets. Alternatively, a thin stream may be formed carrying liquid away from the Taylor cone before the stream is broken up into droplets. In either case, these droplets migrate from the positive emitter towards the mass spectrometer inlet. The droplets undergo solvent evaporation and fission, which allows the generation of gas phase ions. The ions are then introduced into mass spectrometer's vacuum and are subjected to mass spectrometric analysis. Analogously, in the negative-ion mode of operation, the electric field is reversed and the charge of the gas phase ions formed as a result is reversed as well.

The performance of an electrospray emitter is limited in large part by its overall geometry, which in turn is determined by the technique used to fabricate the emitter. For example, several different types of electrospray emitters for use in low flow rate mass spectrometry include a glass tip that is formed by heating and pulling a glass capillary. As a result of such stretching, the outer and inner diameters of such capillaries are decreased.

Additional electrospray emitter shaping techniques include, e.g., mechanical machining methods. Such methods suffer from a number of drawbacks such as low output and inferior dimensional control. While semiconductor surface micromachining fabrication techniques have been proposed, such techniques are not suitable for producing an emitter that protrudes from a lateral surface of a substantially planar device.

Currently, microdevices employing microfluidic technology are used as chemical analysis and clinical diagnostic tools. Sample preparation, separation and detection compartments have been proposed to be integrated on such devices. In general, the small size of microdevices allows for the analysis of minute quantities of a fluid sample, which is an advantage when the sample is expensive or difficult to obtain. See, e.g., U.S. Pat. No. 5,500,071 to Kaltenbach et al., U.S. Pat. No. 5,571,410 to Swedberg et al., and U.S. Pat. No. 5,645,702 to Witt et al. In addition, such microfluidic technologies may operate at extreme low flow rates, e.g., in the nanoflow regime. This tends to increase mass spectrometry sensitivities.

Many have attempted to incorporate electrospray technology in such microdevices. One such effort to interface a microdevice with a mass spectrometer involves providing an outlet on an unbounded surface of a microdevice from which fluid sample is dispersed. See, e.g., U.S. Pat. No. 5,872,010 to Karger et al. and Ramsey et al. (1997), "Generating Electrospray from Microchip Devices Using Electoosmotic Pumping," Anal. Chem. 69: 1174-78. This approach is problematic because it tends to require a larger sample volume, lower ionization efficiency, and/or compromise band resolution emerging from the outlet port. It has been observed that a sharp emitter with a small outside diameter and a smooth rim is generally desired for increasing stability of electrospray ionization, especially at a low sample flow rate.

Several approaches have been reported for integrating electrospray tips onto microdevices. For example, an electrospray emitter formed separately from a microdevice for subsequent attachment. See, e.g., International Patent Publication No. WO 00/022409; Figeys et al. (1997), "A Microfabricated Device for Rapid Protein Identification by Microelectrospray Ion Trap Mass Spectrometry," Anal. Chem. 69:3153-60; Zhang et al. (1999), "A Microfabricated Devices for Capillary Electrophoresis-Electrospray Mass Spectrometry," Anal. Chem. 71:3258-64; Li et al. (2000), "Separation and Identification of Peptide from Gel Isolated Membrane Proteins Using a Micromachined Device for Combined Capillary Electrophoresis," Anal. Chem. 72:799-809; and Zhang et al. (2000), "A Microdevice with Integrated Liquid Junction for Facile Peptide and Protein Analysis by Capillary Electrophoresis/Electrospray Mass Spectrometry," Anal. Chem. 72:1015-22. However, the likelihood of success in implementing this approach depends greatly on the quality of the attachment operation, and the interface formed between the emitter and the microdevice.

Micromachined electrospray emitters have been produced from silicon-based microdevices (see, e.g., International Patent Publication No. WO 98/35376 and Schultz et al. (1999) "A fully integrated monolithic microchip-based electrospray device for microfluidic separations," 47th ASMS Conference on Mass Spectrometry and Allied Topics, June 13-17) and from Parylene-based microdevices (see, e.g., Licklider et al. (2000), "A Micromachined Chip Based Electrospray Source for Mass Spectrometry," Anal. Chem. 72:367-75. However, these approaches also suffer from a number of drawbacks. For example, while silicon ESI emitters can be made with very small tip diameters, integration of such emitters to additional microdevice functionalities can be difficult and costly. In addition, while Parylene processing costs tend to be significantly lower than silicon processing costs, dimensional and geometrical control over Parylene-based emitters is lacking compared to silicon-based emitters.

Laser ablation may be used to form features of microdevices such as those described in U.S. Pat. No. 6,459,080 to Yin et al. For example, commonly owned U.S. patent application Ser. No. 09/711,804 entitled "A Microdevice Having an Integrated Protruding Electrospray Emitter and a Method for Producing the Microdevice," inventors Brennen, Yin, and Killeen, filed on Nov. 13, 2000, describes a method for shaping a polymeric microdevice that involves removing material through a non-mechanical technique, e.g., laser ablation. As a result of material removal, an exterior microdevice surface is formed having an integrated electrospray emitter protruding therefrom. The emitter may be shaped to facilitate the formation of a low volume Taylor cone from the sample emerging from the sample outlet port under influence of an electric field.

While laser ablation is an effective technique for removing material from polymeric microdevices to form ESI emitters, there is a limit to the degree to which the geometric dimensions of emitters may be controlled. Generally, it is difficult to form ESI emitters having an extremely small-diameter tip by removing material from polymeric materials through the use of laser ablation alone. When emitters having uncontrolled geometries are placed in operation, unstable Taylor cones may be formed, especially at low flow rates and at low solvent concentrations.

Thus, there is a need and a desire to improve the performance of microdevices having integrated ESI emitters by providing an improved method for controlling the geometry and dimensional tolerances of the emitters.

SUMMARY OF THE INVENTION

Accordingly, it is an object of the present invention to overcome the above-mentioned disadvantages of the prior art by providing a microdevice having an annular lining that conforms to a downstream surface of a conduit contained in the microdevice.

It is another object of the invention to provide a method for producing the annular lining of the microdevice.

It is still another object of the invention to provide a method to form an integrated electrospray emitter protruding from an exterior surface of a microdevice.

Additional objects, advantages and novel features of the invention will be set forth in part in the description that follows, and in part will become apparent to those skilled in the art upon examination of the following, or may be learned through routine experimentation during the practice of the invention.

In a first embodiment, the invention provides a microdevice constructed from a substrate having a microchannel formed therein and a cover plate arranged over the substrate. The cover plate in combination with the microchannel at least partially defines a conduit within the microdevice. The conduit has a surface that extends from an upstream region toward a downstream region and terminates at an opening. The microdevice also includes an annular lining that conforms to the conduit inner surface at the downstream region and extends from the opening toward the upstream region in the conduit.

Typically, the annular lining has a thickness of no more than about 10 micrometers, and extends from the opening conformingly along the conduit surface for at least about 100 micrometers. In addition, the lining may be comprised of an electrically conductive material, onto which an emitter may be produced in situ by depositing an emitter material on the inner surface of the annular lining.

For example, the microdevice may be produced by first depositing, e.g., via a vapor phase deposition technique such as evaporation or sputtering, a surface-conforming material on a cover plate and in a microchannel formed in a substrate and arranging the cover plate over the substrate. The surface-conforming material forms the annular lining. Emitter material may then be electrodeposited, e.g., electroplated, or deposited via electroless technique, onto the annular lining.

Once a microdevice is formed having an emitter that is located within the conduit and conforms to the conduit surface at the downstream region, material may be removed from the cover plate and/or substrate about the opening. As a result, an exterior microdevice surface is formed and a downstream portion of the emitter is exposed that protrudes from the exterior surface of the microdevice. Material removal may be carried out through various techniques that include, but are not limited to, laser ablation, reactive ion etching, wet or dry chemical etching, and heating.

BRIEF DESCRIPTION OF THE DRAWINGS

FIG. 1A provides an exterior view of the microdevice. FIG. 1B depicts the microdevice in cross-sectional view along the plane indicated by dotted line A and the instability of the Taylor cone.

FIG. 3A illustrates an open microdevice formed from a cover plate and a substrate having a substantially planar surface with a microchannel therein. FIG. 3A' depicts an alternative microdevice to that illustrated in FIG. 3A, wherein the cover plate and substrate are formed from a unitary piece rather than as two separated pieces.

FIG. 5A illustrates the removal of material about an electrospray emitter using two directional sources of electromagnetic radiation from a direction orthogonal to that of the electrospray emitter. FIG. 5B illustrates the removal of material about an electrospray emitter using a directional source of electromagnetic radiation from a direction parallel to that of the electrospray emitter.

DETAILED DESCRIPTION OF THE INVENTION

Figure 1A:
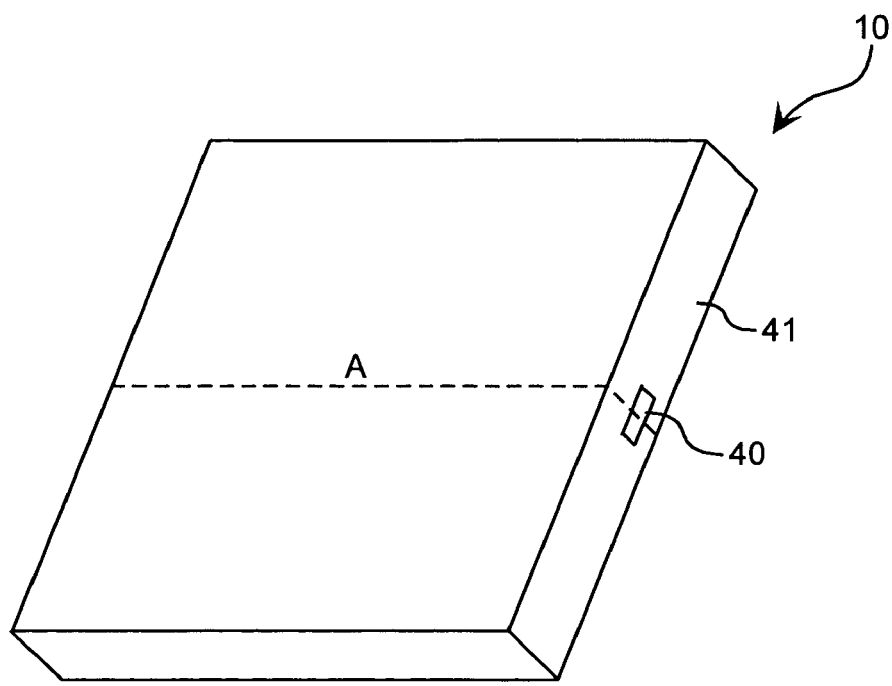
FIGS. 1A and 1B, collectively referred to as FIG. 1, schematically illustrate a known microdevice having an edge electrospray interface.

Before the invention is described in detail, it is to be understood that unless otherwise indicated this invention is not limited to particular materials, components or manufacturing processes, as such may vary.

It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a material" includes a single material as well as a combination of materials, reference to "a conduit" includes one or more conduits, and the like.

In this specification and in the claims which follow, reference will be made to a number of terms which shall be defined to have the following meanings:

As used herein, the term "biofouling" refers to uncontrolled accumulation of biomaterials such as proteins, protein fragments, or other biomaterials present in a sample or reaction fluids that attaches or adheres to an interior surface of a microdevice. Thus, the term "biofouling resistant" refers to a material that resists such accumulation of biomaterials.

The term "conduit" as used herein refers to a three-dimensional enclosure through which fluid may be transported, and is formed by one or more walls and that extends from one or more terminal openings to one or more other terminal openings. The term "channel" is used herein to refer to an open groove or a trench in a surface. A channel in combination with a solid piece over the channel may form a conduit. Conduits and channels are "fluid-transporting features," i.e., an arrangement of solid bodies or portions thereof that direct fluid flow. Fluid-transporting features include, but are not limited to, chambers, reservoirs, conduits, and channels.

The term "integrated" is used to refer to an item that is permanently joined to another to form a unitary item. For example, a substrate having an integrated electrospray emitter means that substrate and the electrospray emitter form a monolithic item and that the substrate and the emitter are not readily detachable at the interface formed therebetween. Thus, the term "integrated electrospray emitter" does not encompass a preformed emitter mechanically inserted into a microdevice.

The prefix "micro" as used in the term "microdevice" refers to a device having features of micron or submicron dimensions, and which can be used in any number of chemical processes or fluid transport techniques involving very small amounts of fluid. Such processes and techniques include, but are not limited to, electrophoresis (e.g., CE or MCE), chromatography (e.g., micro- or nano-LC), screening and diagnostics (using, e.g., hybridization or other binding means), and chemical and biochemical synthesis (e.g., DNA amplification as may be conducted using the polymerase chain reaction, or "PCR"). The features of the microdevices are adapted to the particular use. For example, microdevices may contain a microconduit on the order of 1 μm to 200 μm in diameter, typically 5 μm to 75 μm, when the cross sectional shape of the microconduit is circular, and approximately 1 mm to 100 cm in length. Other cross-sectional shapes, e.g., rectangular, square, triangular, pentagonal, hexagonal, etc., having dimensions similar to above may be employed as well. In any case, such a microconduit may have a volume of about 1 pl to about 100 μl, typically about 1 nl to about 20 μl, more typically about 10 nl to about 1 μl.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not. Mere reference to a feature, structure, event or circumstance as "optional," does not imply in any way whether the feature, structure, event or circumstance is be preferred.

The term "substantially" as in "substantially identical in size" is used herein to refer to items that have the same or nearly the same dimensions such that corresponding dimensions of the items do not differ by more than approximately 15%. Preferably, the corresponding dimensions do not differ by more than 5% and optimally by not more than approximately 1%. For example, two openings are substantially identical in size when the openings exhibit dimensions within approximately 10% of each other. Other uses of the term "substantially" have an analogous meaning.

In general, the invention relates to the production of microdevice having an integrated electrospray emitter that protrudes from an exterior surface of the microdevice. A microdevice may be provided comprising a substrate having a microchannel formed therein and a cover plate arranged over the substrate. The cover plate in combination with the microchannel at least partially defines a conduit within the microdevice, wherein the conduit has a surface that extends from an upstream region toward a downstream region and terminates at an opening. Also included is an annular lining that conforms to the conduit surface at the downstream region and extends from the opening toward the upstream region in the conduit. Once the microdevice is assembled, an emitter material is deposited on the annular lining. As a result, an integrated emitter is formed in the downstream region of the conduit. When material is removed from the cover plate and/or substrate about the opening, an exterior microdevice surface is formed. Material removal may also expose a downstream portion of the emitter that protrudes from the exterior surface. Alternatively, no emitter material is deposited on the annular lining and the annular lining itself serves as the integrated emitter.

Figure 1B:
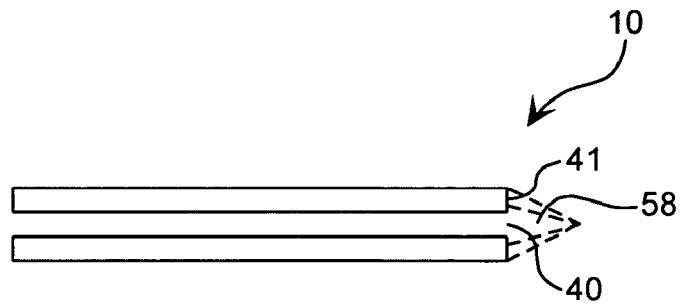

In order to fully elucidate the novel and nonobvious aspects of the invention, FIG. 1 is provided to highlight the differences between known and inventive electrospray technology described herein. FIG. 1 depicts an electrospray interface at an edge of a microdevice described in U.S. Pat. No. 5,872,010 to Karger et al. As is the case with all figure referenced herein, in which like parts are referenced by like numerals, FIG. 1 is not to scale, and certain dimensions may be exaggerated for clarity of presentation. As illustrated in FIG. 1, the microdevice 10 is provided having an edge electrospray interface in the form of an outlet port 40 located at a substantially planar exterior surface 41 of the device 10. The outlet port 40 has a relative small cross-sectional area compared with the area of surface 41. A Taylor cone 58 is formed when fluid emerging from outlet port 40 is placed under an electric field. As depicted in FIG. 1B, however, the size of the Taylor cone 58 may vary (as indicated by the dashed lines), leading to an unstable Taylor cone.

Figure 2:
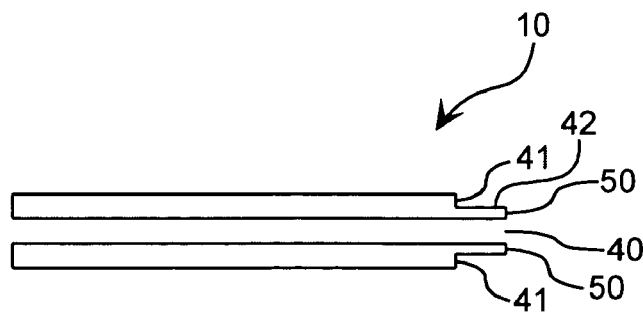
FIG. 2 depicts a microdevice in cross-sectional view having an idealized geometry for an electrospray emitter.

In contrast, FIG. 2 schematically depicts a microdevice having an idealized configuration. The microdevice 10 has a generally emitter 42 protruding from an exterior surface 41 thereof. Outlet port 40 is located at the terminal surface 50 of the emitter 42. As depicted, the outlet port 40 is generally circular in shape and has a diameter only slightly smaller than the outer diameter of the emitter 42. Accordingly terminal surface 50 has a very small surface area, and fluid emerging from the outlet port 40 under an electric field tends to form a stable, low volume Taylor cone.

Figure 3A:
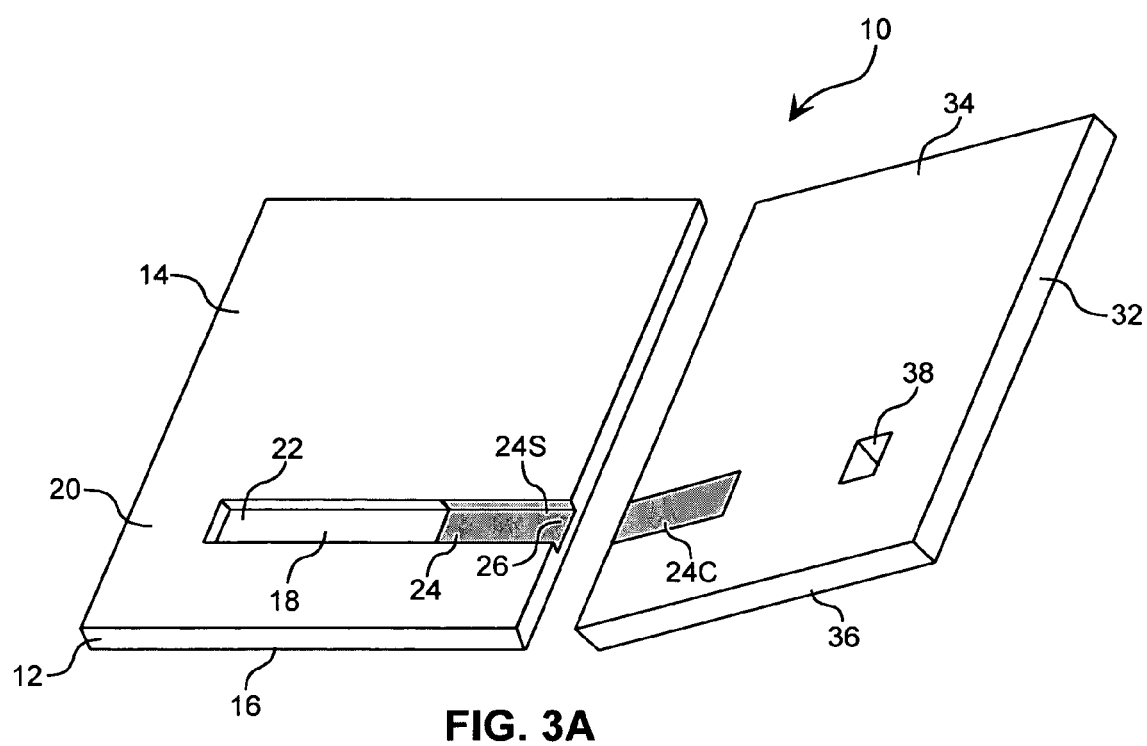
FIGS. 3A, 3A', 3B, 3C, 3D and 3E, collectively referred to as FIG. 3, illustrate a method for producing an integrated electrospray emitter of a microdevice.

The invention provides a method for producing an integrated electrospray emitter of a microdevice that exhibits the idealized configuration depicted in FIG. 2. FIG. 3 provides an exemplar of such a method. In this embodiment, a microdevice 10 is formed from a substrate 12 and a cover plate 32. FIG. 3A illustrates the microdevice 10 in an open form. The substrate 12 generally comprises first and second substantially planar opposing surfaces indicated at 14 and 16, respectively. The substrate 12 has a microchannel 18 in the first planar surface 14. The microchannel has an upstream region 20 that terminates at an inlet terminus 22 and a downstream region 24 that terminates at terminus 26 located at an edge of the substrate surface 14. It will be readily appreciated that although the microchannel 18 has been represented in a generally extended form, microchannels can have a variety of configurations, such as in a straight, serpentine, spiral, or any tortuous path desired. Further, the microchannel 18 can be formed in a variety of channel cross-section geometries including semi-circular, rectangular, rhomboid, and the like, and the channels can be formed in a wide range of aspect ratios. It is also noted that a device having a plurality of microchannels thereon falls within the spirit of the invention. Optionally, the first planar surface 14 of the substrate may include other features such as cavities, orifices, additional microchannels and the like depending on the desired function(s) of the microdevice. Such features may be formed in any geometry and with any aspect ratio, limited only by the overall thickness of the substrate. A layer of electrically conductive material is selectively deposited on the portion of the substrate surface 14 that corresponds to the downstream region of the channel 18. As a result, an electrically conductive lining layer 24S is formed that conforms the surface of channel at the downstream region.

The cover plate 32 is provided having opposing surfaces 34 and 36, wherein surface 34 is substantially planar and capable of interfacing in a fluid-tight manner with the first planar surface 14 of the substrate 12. An inlet port 38 is depicted extending through surfaces 34 and 36. As is the case with the substrate surface 14, surface 34 of the cover plate 32 may include other features such as cavities, orifices, microchannels. A layer of electrically conductive material is selectively deposited to on the portion of the cover plate surface 34 that corresponds to the lining layer 24S of the substrate to form lining layer 24C. As shown, the lining layer 24C conforms to the surface 34. Deposition of the electrically conductive material may be carried out through any technique effective to ensure that the lining layers 24S and 24C meet the dimensional criteria set forth below. For example, as discussed infra, the electrically conductive material may serve as a surface onto which additional material may be electrodeposited. Thus, vapor phase deposition techniques such as evaporation or sputtering may be used to deposit a metallic coating to form layers 24S and 24C.

As shown in FIG. 3A, the cover plate 32 may be formed from a discrete component separate from the substrate 12. In general, a discrete cover plate may require microalignment means to align the cover plate with the substrate to ensure precise microalignment of microfabricated features in a microdevice. Microalignment means can be formed either by laser ablation or by other methods of fabricating shaped pieces well known in the art. Representative microalignment means that can be employed herein include a plurality of co-axially arranged apertures microfabricated in component parts and/or a plurality of corresponding features substrates, e.g., projections and mating depressions, grooves and mating ridges or the like. Alternative alignment means includes, but are not limited to, features forms in component parts such as pin and mating apertures.

Alternatively, as shown in FIG. 3A', the substrate and the cover plate may be formed in a single, solid flexible piece. See e.g., U.S. Pat. No. 5,792,943 to Craig. The flexible substrate includes first and second portions, corresponding to the substrate 12 and the cover plate 32, wherein each portion has a substantially planar interior surface. The first and second portions are separated by at least one fold means, generally indicated at 30, such that the portions can be readily folded to overlie each other. The fold means 30 can comprise a row of spaced-apart perforations ablated in the flexible substrate, a row of spaced-apart slot-like depressions or apertures ablated so as to extend only part way through the flexible substrate, or the like. The perforations or depressions can have circular, diamond, hexagonal or other shapes that promote hinge formation along a predetermined straight line. The fold means 30 serves to align the cover plate 32 with the substrate 12.

Like the substrate, the cover plate of the above described device can also include a variety of features such as apertures, microchannels, cavities, which have been formed therein (not shown). For example, if there is desired to form a conduit having a circular cross-section, mating microchannels each having a semicircular cross-sectional area may be formed on the contact surfaces of the cover plate and the substrate. Such mating microchannels, in combination with each other may form a conduit having a circular cross-section.

The materials used to form the substrate and cover plate in the microdevice of the invention as described above are selected with regard to physical and chemical characteristics that are desirable for sample handling and electrospray. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser machining, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto. For example, polymer channels can be formed on the surface of a substrate using photo-imageable polyimide. Also, all device materials used should be substantially chemically inert and physically stable with respect to any substance with which they come into contact (e.g., with respect to pH, electric fields, etc.). For example, microdevices suitable for use with biochemical analysis should be biofouling resistant.

Typically, the substrate and/or cover plate are comprised of an electrically insulating material. Polymeric materials are particularly preferred herein, and will typically be organic polymers that are homopolymers or copolymers, naturally occurring or synthetic, crosslinked or uncrosslinked. Specific polymers of interest include, but are not limited to, polyimides, polyketones, polysulfones, polycarbonates, polyesters, polyamides, polyethers, polyurethanes, polyfluorocarbons, polystyrenes, polyacrylonitrile, polybutadiene, polystyrene, acrylate and acrylic acid polymers such as polymethyl methacrylate, silicones, substituted and unsubstituted polyolefins, and copolymers thereof. Polyimides and polyketones are of particular interest due to their resistance to biofouling and are a highly desirable substrate material in a number of contexts. Polyimides are commercially available, e.g., under the tradename Kapton®, (DuPont, Wilmington, Del.) and Upilex® (Ube Industries, Ltd., Japan). In addition, polyetheretherketone (PEEK) has been found to exhibit excellent resistance to biofouling and is therefore a preferred polyketone. However, other electrically insulating materials may be used as well. For example, ceramics (including aluminum oxide and the like) and glasses (silicates, borosilicates, and the like) are generally considered electrically insulating. In addition, or in the alternative, the substrate and/or cover plate may be comprised of an electrically conductive material. For example, any of a number of metals or carbonaceous materials may be used to form a conductive cover plate and/or the substrate.

The substrates and cover plates of the invention may also be fabricated from a composite, i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, available from DuPont (Wilmington, Del.), that has been co-extruded with a second, thin layer of a thermal adhesive form of polyimide known as KJ®, also available from DuPont (Wilmington, Del.).

The features of the microdevice, e.g., fluid-transporting features, microalignment features, etc., may be formed using any method suitable for microdevice fabrication, including, but not limited to, micromolding and casting techniques, embossing methods, surface micro-machining and bulk-micromachining. The latter technique involves formation of microstructures by etching directly into a bulk material, typically using wet chemical etching or reactive ion etching ("RIE"). Surface micro-machining involves fabrication from films deposited on the surface of a substrate. An exemplary surface micro-machining process is known as "LIGA." See, e.g., Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35-36; Ehrfeld et al. (1988), "1988 LIGA Process: Sensor Construction Techniques via X-Ray Lithography," *Tech. Digest from IEEE Solid-State Sensor and Actuator Workshop,* Hilton Head, S.C.; Guckel et al. (1991) *J. Micromech. Microeng.* 1: 135-138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—i.e., diameters—on the order of microns.

Figure 3B:
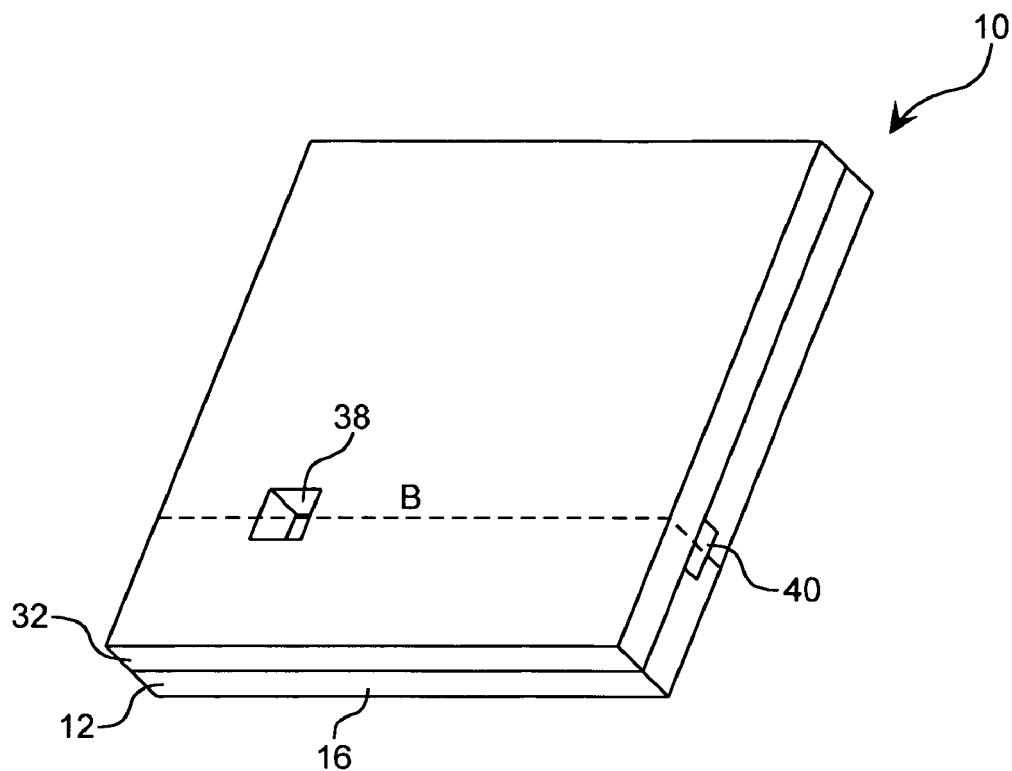
FIG. 3B illustrates the microdevice of FIGS. 3A and 3A' in a closed form wherein the cover plate is aligned with and placed against the substantially planar surface of the substrate.

As shown in FIG. 3B, the cover plate 32 is arranged over substrate surface 14. The cover plate surface 34 placed over surface 14 such that fluid-tight contact is achieved between surfaces 14 and 34. Fluid-tight contact may be achieved using pressure sealing techniques, by using external means to urge the pieces together (such as clips, tension springs or associated clamping apparatus), or by using adhesives well known in the art of bonding.

It should be noted that the invention is not limited to two-layer devices such that the microdevice depicted in FIG. 3. For example, a microdevice having the same conduit arrangement as that depicted in FIG. 3, may be formed from three (or more) layers. This may be achieved by interposing a middle layer containing a channel-shaped cutout between two substantially planar cover plates.

Figure 3C:
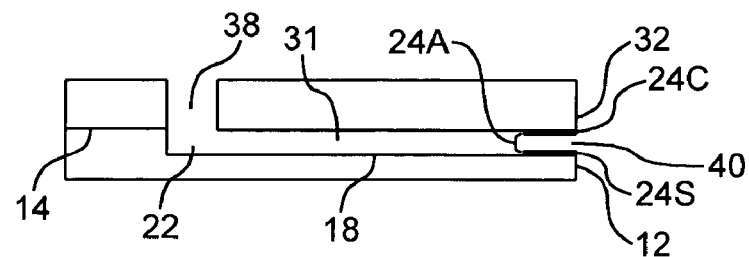
FIG. 3C illustrates the microdevice of FIG. 3B in cross sectional view along dotted line B.

As illustrated in schematic cross sectional view, FIG. 3C depicts an arrangement of cover plate 32 over the substrate surface 14 results in the formation of microconduit 31. Microconduit 31 is defined by the microchannel 18 in combination and the cover plate contact surface 34. Inlet port 38 is aligned with the inlet terminus 22. Lining layers 24S and 24C together forms an annular lining 24A that conforms to the surface of microconduit 31.

It should be noted that any of the above feature-forming techniques may also be used to provide for features of sufficiently high definition, i.e., microscale components, channels, chambers, etc., such that precise alignment—"microalignment"—of these features is possible, i.e., the laser-ablated features are precisely and accurately aligned, including, e.g., the alignment of complementary microchannels or microcompartments with each other, inlet and/or outlet ports with microcolumns or reaction chambers, detection means with microcolumns or separation compartments, detection means with other detection means, projections and mating depressions, grooves and mating ridges, and the like.

As alluded to above, the annular lining serves as a base layer onto which additional may be deposited to form an emitter. Accordingly, the lining is provided in accordance with the desired emitter configuration. For example, the annular lining may serve as an electrode onto which material may be electrodeposited. In such a case, annular lining is comprised of an electrically conductive material. Such electrically conductive materials are typically comprised of one or more metals because of their high electrical conductivity. Suitable metals include, for example, aluminum, chrome, titanium, silver, nickel, palladium, platinum, chromium, molybdenum, tungsten. In addition or in the alternative, the electrically conductive material may be comprised of a polymer such as polyaniline, polypyrrole and poly(3,4-ethylenedioxy-2,5-thiophene). Furthermore, certain ceramic materials may be used to form the annular lining. Such ceramic materials include, for example, conductive metal oxides such as ReO, TiO, ZnO, $CrO_2$, $V_2O_3$ and various forms of indium tin oxide and conductive transition metal nitrides such as titanium nitride, zirconium nitride, and chromium nitride. Optionally, the annular lining may be comprised of a plurality of layers, e.g., an adhesion promoting layer interposed between the conduit surface and a conducting layer.

The thickness of the annular lining may vary. Typically, the annular lining has a thickness of no more than about 10 micrometer. Often, thickness is no more than about 1 micrometer. Preferably, the annular lining has a uniform thickness of about 5 nanometers to about 500 micrometers. As alluded to above, such thicknesses may be achieved through vapor phase deposition techniques such as evaporation or sputtering.

As shown, the annular lining 24A is located within a downstream region of the microconduit 31 and extends from outlet port 40 toward the upstream region in the microconduit 31. For example, the annular lining extends in an upstream direction conformingly along the conduit surface for at least about 100 micrometers. More preferably, the annular lining extends conformingly along the conduit surface for at least about 1 millimeter.

Figure 3D:
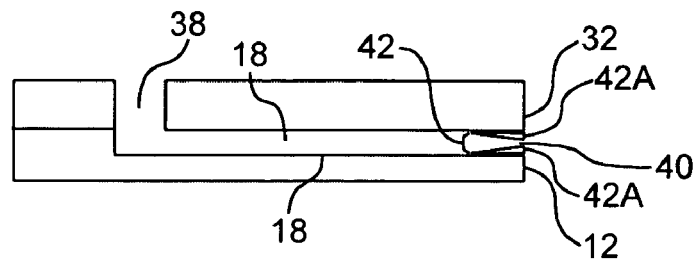
FIG. 3D illustrates the deposition of emitter material onto the annular lining of the microdevice of 3D.

As depicted in FIG. 3D, an optional additional emitter material 42A may be deposited on the annular lining 24A. The emitter material 42A may be the same or a different material as that used to form the annular lining 24A. As a result, an integrated emitter 42 is formed in situ. Typically, the integrated emitter 42 has a wall thickness of no more than about 100 micrometers. Preferably, the wall thickness is no more than about 25 micrometers. Optimally, the wall thickness is no more than about 10 micrometers. However, additional emitter material may not be needed if the annular lining is of sufficient thickness.

Any of a number of material deposition processes known in the art may be employed. Typically, additional emitter material is deposited through an electrodeposition technique. For example, a metal may be electroplated onto the annular lining. This may be carried out by electrically connecting the annular lining to a current source and providing a plating solution in the microconduit 31. Optionally, the plating solution flows either in an upstream direction from the outlet port 40, or in a downstream direction from inlet port 38 during plating. Because the emitter material is depleted from the plating solution during deposition, the direction and velocity of plating solution flow may be used to control the wall thickness profile of the emitter 42. As depicted in FIG. 3D, the wall thickness of emitter 42 decreases along its length upstream from the outlet port 40. Such a wall thickness profile may be achieved by flowing plating solution in an upstream direction through the microconduit 31 at a sufficiently slow rate that such emitter material is depleted from the solution along the length of the emitter in an upstream direction.

Once the emitter is formed, material is removed from the cover plate and/or substrate to form an exterior microdevice surface and to expose a downstream portion of the emitter that protrudes from the exterior surface. Because it is desirable for the emitter to be solidly anchored in the microconduit and to form a leak-free interface with the conduit surface, a substantial portion of the emitter typically remains within the microdevice, i.e., in the microconduit, after material is removed from the microdevice. The exterior surface of the exposed portion emitter corresponds to the luminal surface of the portion of microconduit defined by the removed microdevice material.

Any of a number of material removal techniques may be used. For example, material removal may be carried out through reactive ion etching, wet or dry chemical etching, application of heat, or through mechanical abrasion. Given the size and the fragility of the emitters, each of these material removal techniques exhibits some drawbacks. For example, mechanical machining offers inferior control over the dimensions of the materials removed and may damage the emitter. Similarly, while heat may be applied to the cover plate and/or the substrate to melt away material about the emitter, dimensional control is also lacking.

To improve dimensional control over material removal, masking techniques such as those employed in conjunction with semiconductor fabrication techniques may be used. However, ordinary semiconductor fabrication methods are generally not well suited for high volume large-size parts desirable for certain microdevices applications. They are relatively slow and have stringent limits on materials that may be used during their practice. As an additional concern, chemicals used in photoresist masking are highly toxic and harmful to the environment. Consequently, producing electrospray emitters using photoresists involves high waste disposal cost and poses a potential health hazard. Such drawbacks are detailed in U.S. patent application Ser. No. 09/711,804.

Because of the disadvantages associated with use of photoresist, the preferred material removal technique does not require use of photoresist in order to shape the electrospray emitter with dimensional precision. Laser ablation does allow for dimensionally precise shaping of the electrospray emitter and is therefore a preferred material removal technique for producing the integrated emitter of the present microdevice. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation may involve the use of a high-energy photon laser such as an excimer laser of the $F_2$, ArF, KrCl, KrF, or XeCl type. However, other ultraviolet light sources with substantially the same optical wavelengths and energy densities may be used as well. For example, solid-state, diode pumped ultraviolet lasers may be used. Laser ablation techniques are described, for example, by Znotins et al. (1987) *Laser Focus Electro Optics,* at pp. 54-70, and in U.S. Pat. Nos. 5,291,226 and 5,305,015 to Schantz et al. Laser ablation is also preferred for forming features of the microdevice other than the protruding electrospray emitter.

Another technique to form the electrospray emitter is through photochemical etching. Photochemical etching is a process in which a solid member is exposed to a chemical etchant. The etchant does not significantly remove material from the solid member unless light is present. Thus, by immersing the solid member in the etchant and directing light, e.g., by using a laser, to areas of the solid member from which material removal is desired, the electrospray emitter of the invention may be formed without use of photoresist.

Figure 3E:
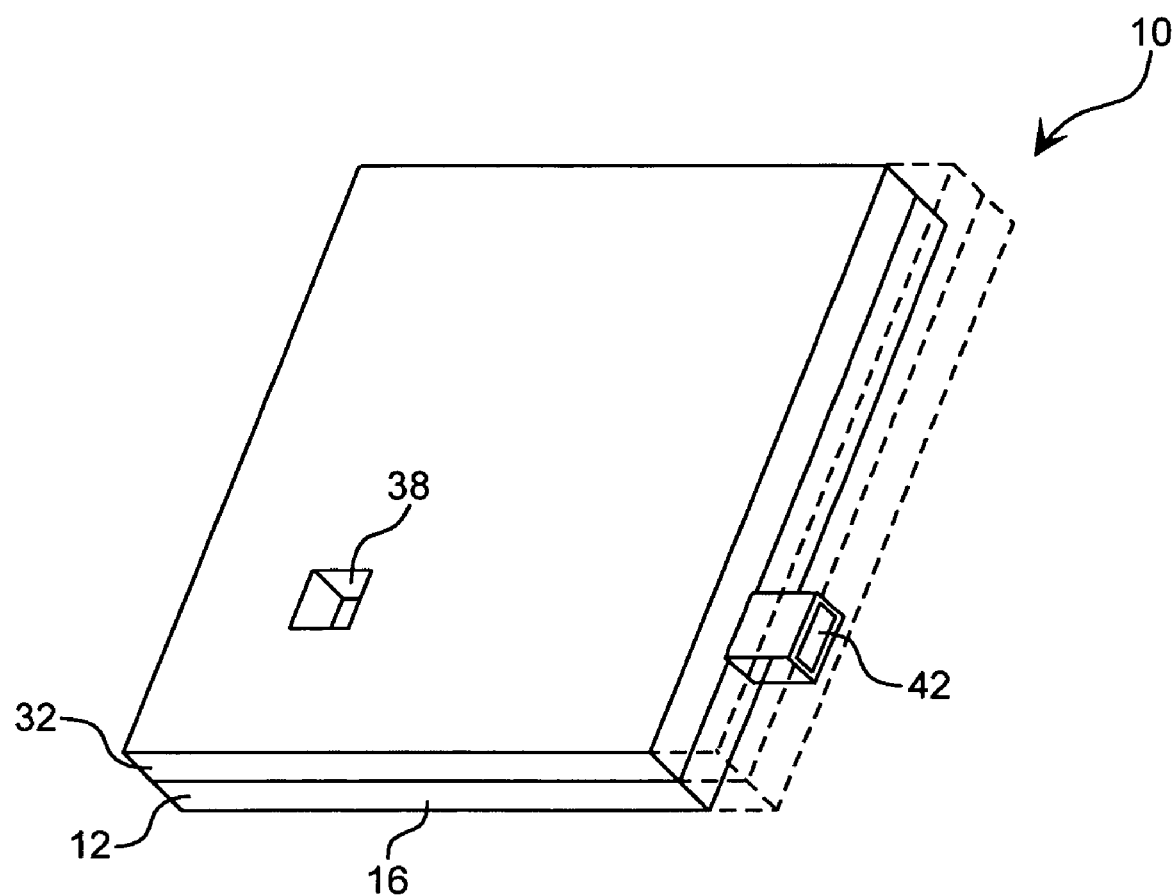
FIG. 3E illustrates the microdevice having material removed therefrom to form an integrated electrospray emitter protruding from a freshly exposed exterior microdevice surface.

FIG. 3E shows the removal of material form both the substrate and the cover plate. Dotted lines indicate the location of material removed from the microdevice. Removal of the material forms a new exterior microdevice surface 41 and exposes the downstream portion of the electrospray emitter 42. The inventive method provides that material is removed. As shown, the electrospray emitter has a square cross-sectional area. However, the emitter may be of any desired shape or geometries as discussed below. As a result, the method forms a microdevice 10 having a protruding and integrated electrospray emitter 42 for introducing a fluid sample into a spray chamber, e.g., to carry out mass spectrometry via electrospray ionization.

Figure 4:
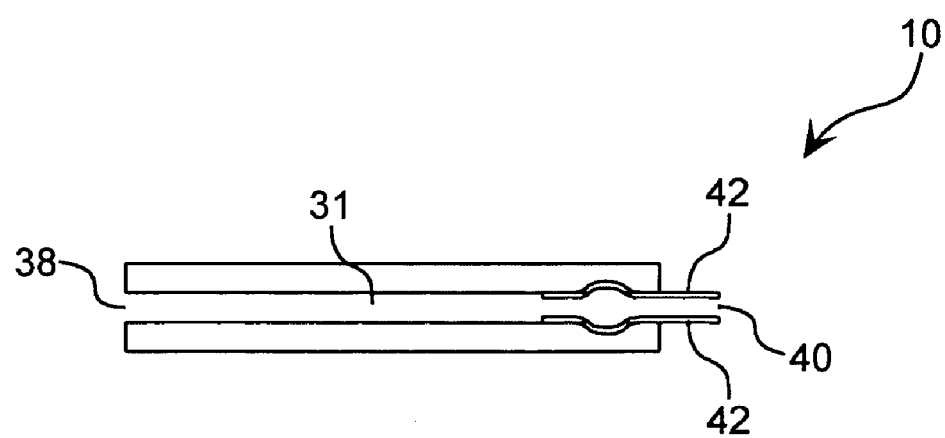
FIG. 4 illustrates in cross sectional view of an embodiment of the inventive microdevice having an internally bulging emitter.

As discussed above, it is desirable for the emitter to be solidly anchored in the microconduit and to form a leak-free interface with the conduit surface. The emitter should resist detachment from the microdevice under forces arising from fluid flow within the microconduit within which the emitter is located. Thus, FIG. 4 illustrates in cross sectional view of an alternative embodiment of the inventive microdevice 10 having a microconduit 31 having a bulging region is located at a downstream region microconduit 31. As shown, the emitter 42 conforms to the surface of the bulging region. It should be apparent that the shape of the emitter helps the emitter 42 resist separation from the microconduit 31 when fluid flows through the microdevice 10 from inlet port 38 to outlet port 40.

Figure 5A:
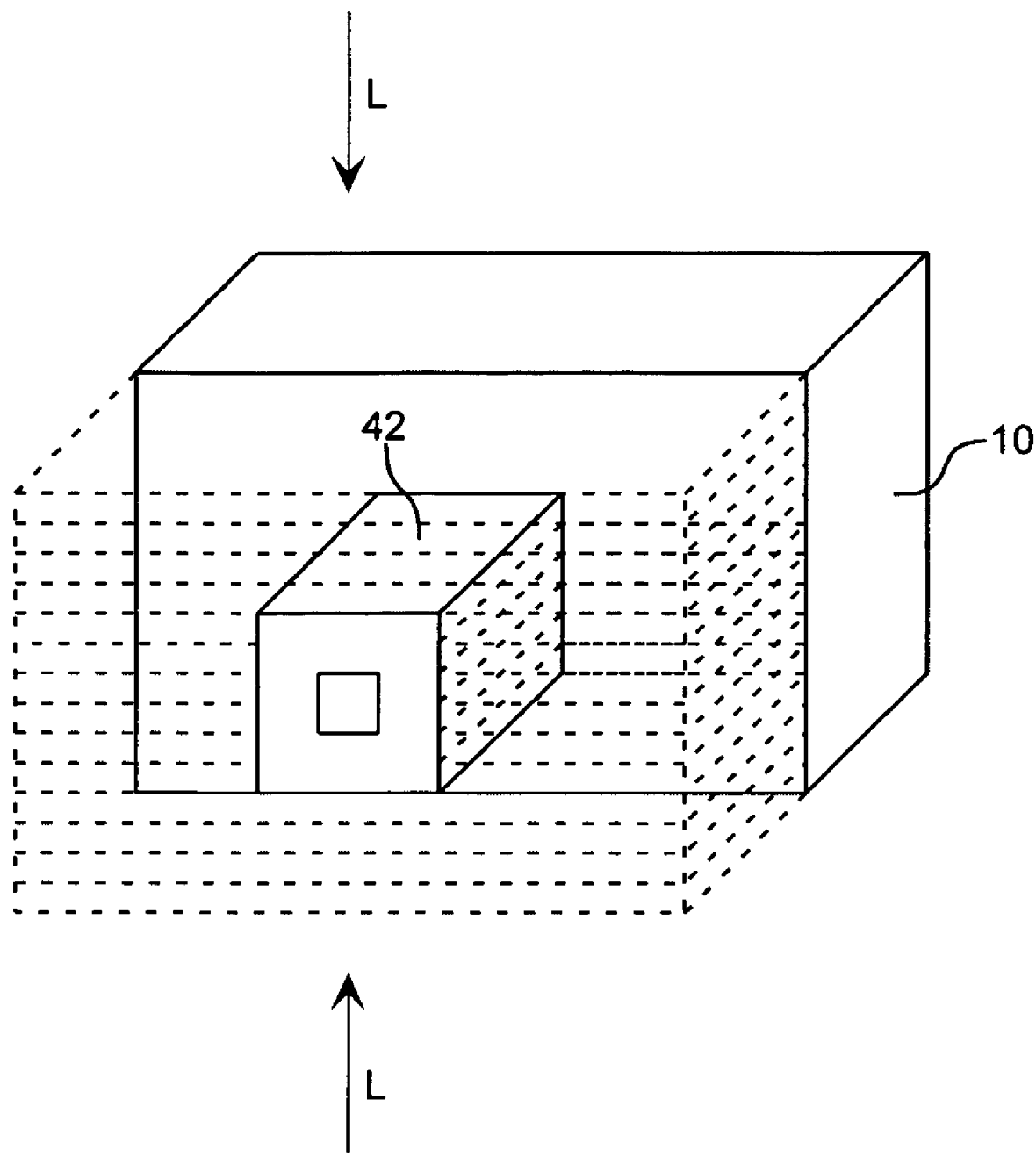
FIGS. 5A and 5B, collectively referred to as FIG. 5, illustrate material removal from a microdevice to expose a protruding portion of an electrospray emitter.
Figure 5B:
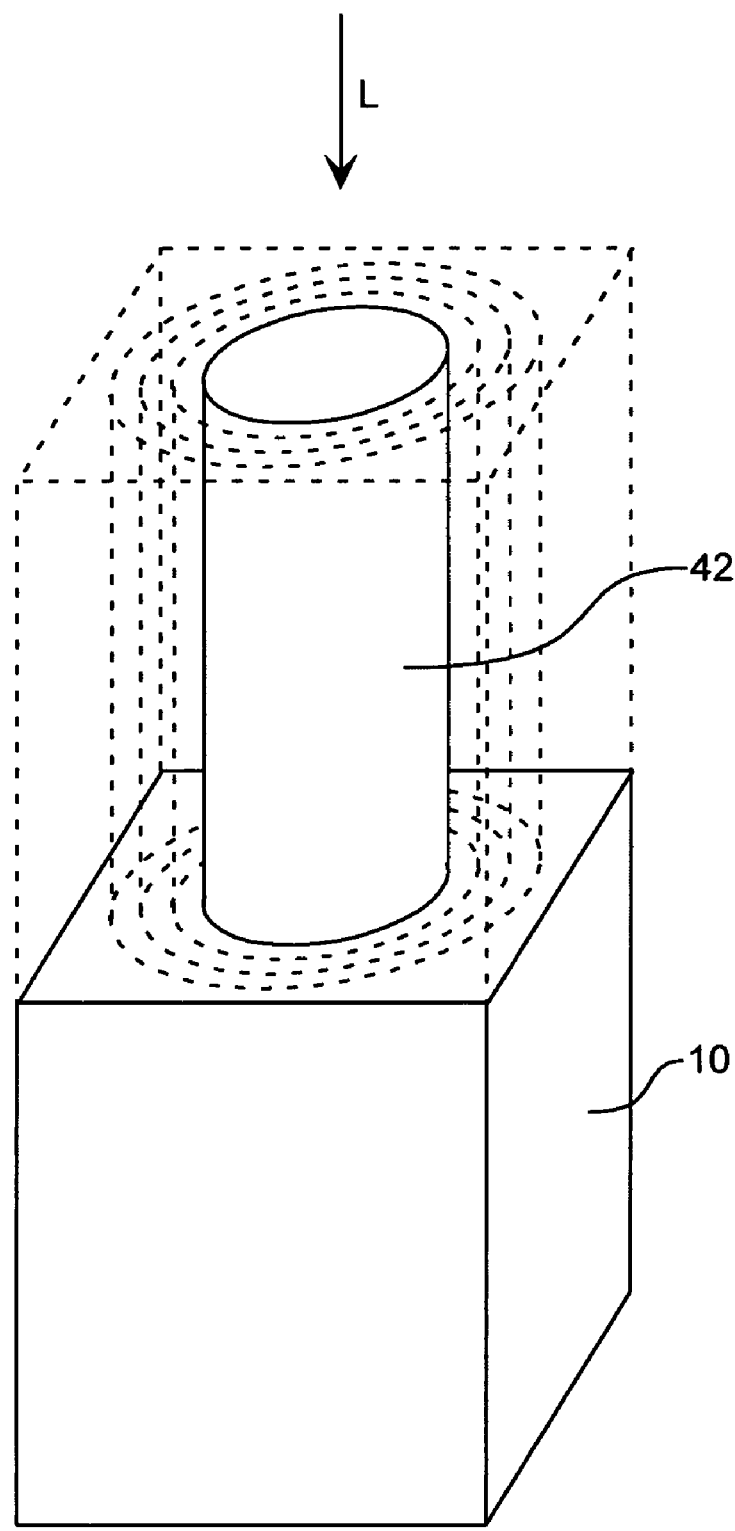

FIG. 5 illustrates two ways in which one or more sources of electromagnetic radiation may positioned in order to remove material from a solid member to shape the integrated electrospray emitter. As used herein, solid member refers to the cover plate, the substrate or a single or multiple-layered structure that includes the cover and/or the substrate. Using the preferred method of laser ablation as an example, electrospray emitters may be exposed in a manner similar to the operation of a standard milling machine for material removal. FIG. 5A illustrates an integrated electrospray emitter 42 protruding from a microdevice 10 and having a square cross-sectional area. The emitter is exposed using laser ablation from a direction orthogonal to the direction of protrusion. Two lasers may be positioned in an opposing manner to remove successive layers from a solid member as indicated by arrows L to form the electrospray emitter 42. Dotted lines indicate the location of removed layers. Alternatively, one laser may be used to remove successive layers as above but from one direction at a time. As still another alternative, material may be removed using only one laser in a direction parallel to that of the ultimately formed electrospray emitter. For example, FIG. 5B illustrates an integrated electrospray emitter 42 protruding from a microdevice 10 and having a circular cross-sectional area. The emitter is shaped using laser ablation from a direction, indicated by arrow L, parallel to the direction of protrusion. Each laser pulse during an increment in time cuts a bit of the material thereby forming the emitter. Successive cylindrical sections are removed as indicated by the dotted lines until the only the emitter remains. It should be evident exposing the electrospray emitter may require moving either the microdevice, the laser, or both in a specified manner in order to ensure proper material removal. Optimally, the laser has an intensity and/or frequency that is sufficiently energetic to remove the substrate and/or cover plate material but insufficiently powerful to remove the emitter material.

Using the material removal techniques as described above, a microdevice may be formed having an ESI emitter. The integrated electrospray emitter may be shaped to facilitate formation of a low volume Taylor cone as well as to provide an acceptable geometry to facilitate optimal ionization of the sample. Exemplary geometries are described in U.S. patent application Ser. No. 09/711,804.

In operation, the microdevice is operatively connected to a spray chamber or an entrance orifice thereof (not shown), and fluid sample from the external source flows in a sample flow path that travels, in order, through the inlet port, the conduit and the sample outlet port on the electrospray emitter and into the spray chamber. The electrospray emitter, regardless of geometry, is subjected to an electric field located between the microdevice and the sample introduction orifice for an analytical device. The electric field at the emitter tips overcomes liquid surface tension of the bulk fluid at the tip such that fine charged droplets separate from the bulk fluid and subsequently move in accordance with their electric charge and the surrounding electric field. That is, the sample becomes charged and dispersed into droplets as it emerges from the sample outlet port and into the spray chamber. Optionally, drying gas is provided to help evaporate the droplets to form gaseous ions.

Optionally, a surface energy modifying coating may be provided on the emitter to further reduce wicking or other unwanted fluid flow on the exterior surface of the emitter. As a further option, when the emitter is nonconductive, a portion of the entirety of the exterior emitter surface may be coated with a conductive material. The conductive material serves to assist the spraying process. While the conductive material may be polymeric or ceramic, polymeric and ceramic materials usually exhibit a lower conductivity than metals. Thus, metals are a preferred conductive coating material for the electrospray emitter. The coating may contain one or more metallic elements. Preferably, the coating is also inert with respect to the sample and may comprise, e.g., gold, platinum, chromium, nickel and other elements that tend exhibit high chemical inertness. The coating may be applied through any of a number of methods known to one of ordinary skill in the art and include, but are not limited to, electroplating, electron-beam sputtering, magnetronic sputtering, evaporation, electroless deposition, and solvent coating.

Thus, in general, the invention provides an improved method for forming a microdevice having a small protruding mass spectrometry ESI emitter having an exacting dimensional tolerance. Such an emitter allows stable, low-volume Taylor cones to be formed from fluid emerging therefrom at very low flow rates. As a result, greater mass spectrometry sensitivity may be achieved.

The invention also allows for integration of additional functionality onto the microdevice. For example, fluid samples, before delivery to an emitter, can be processed through sample preparation steps such as filtration, concentration, or extraction on-device. Such sample preparation steps may be carried out using miniaturized reactors. Any of the ablated features may be constructed to function as a miniaturized reactors and to conduct chemical or biochemical processes. For example, the microchannel may be used, e.g., as a concentrating means in the form of a microcolumn to increase the concentration of a particular analyte or chemical component, as a microreactor for preparative chemical or biochemical processes such as labeling, protein digestion, and the like, or as a purification means to remove unwanted components, unreacted materials, etc. from the reaction chamber following completion of chemical processing. In any case, a motive force may be employed to enhance sample movement from the sample inlet terminus to the sample outlet terminus. The motive force may be adjusted for the particular chemical or biochemical processes that are carried out by the microdevice.

Variations on the present invention will be apparent to those of ordinary skill in the art. For example, it should be evident that a combination of material removal techniques may be employed in order to expose the electrospray emitter. In addition, because fluid flow control is an important aspect of the inventive microdevice and its use, known means for fluid control may represent integrated and/or additional features of the inventive microdevice. Such fluid flow control means include, but are not limited to, valves, motive force means, manifolds, and the like. Such fluid flow control means may represent an integrated portion of the inventive microdevices or modular units operably connectable with the inventive microdevices. It should be further evident that additional substrates may be included to form a multilayered network of conduits for conveying fluid.

While the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

What is claimed is:

1. A microdevice comprising:
   a substrate having a microchannel formed therein;
   a cover plate arranged over the substrate such that the cover plate in combination with the microchannel at least partially defines a conduit within the microdevice, wherein the conduit has a surface that extends from an upstream region toward a downstream region and terminates at an opening; and
   an annular lining that conforms to the conduit surface at the downstream region and extends from the opening toward the upstream region in the conduit.

2. The microdevice of claim 1, wherein the annular lining has a thickness of no more than about 10 micrometer.

3. The microdevice of claim 1, wherein the annular lining extends from the opening conformingly along the conduit surface for at least about 100 micrometers.

4. The microdevice of claim 3, wherein the annular lining extends from the opening conformingly along the conduit surface for at least about 1 millimeter.

5. The microdevice of claim 1, wherein the annular lining is comprised of an electrically conductive material.

6. The microdevice of claim 5, wherein the electrically conductive material is comprised of a metal.

7. The microdevice of claim 5, wherein the electrically conductive material is comprised of a polymer.

8. The microdevice of claim 1, further comprising an integrated emitter in the downstream region of the conduit.

9. The microdevice of claim 8, wherein the emitter is produced in situ by depositing an emitter material on the annular lining.

10. The microdevice of claim 9, wherein the emitter material is comprised of a metal.

11. The microdevice of claim 10, wherein the emitter has an exposed downstream portion that protrudes from an exterior surface of the cover plate and/or the substrate.

12. The microdevice of claim 8, wherein the emitter has a wall thickness of no more than about 100 micrometers.

13. The microdevice of claim 1, wherein the annular lining has an exposed downstream portion that protrudes from an exterior surface of the cover plate and/or the substrate and serves as an integrated emitter.

14. The device of claim 1, wherein the substrate and/or cover plate are comprised of a biofouling resistant material.

15. The device of claim 1, wherein the substrate and/or cover plate are comprised of an electrically insulating material.

16. The device of claim 15, wherein the electrically insulating material is a polymeric material.

17. The device of claim 16, wherein the polymeric material is selected from the group consisting of polyimides and polyketones.

18. The device of claim 16, wherein the material is selected from the group consisting of polycarbonates, polyesters, polysulfones, polyamides, polyethers, polyurethanes, polyfluorocarbons, polystyrenes, polyacrylonitriles, polybutadienes, polystyrenes, acrylate and acrylic acid polymers, polyolefins, silicones, mixtures thereof and copolymers of any of the foregoing.

19. The device of claim 15, wherein the electrically insulating material is a glass and/or ceramic material.

20. The device of claim 1, wherein the substrate and/or cover plate are comprised of an electrically conductive material.

21. A method for producing a microdevice, comprising:
   (a) depositing a surface-conforming material on a cover plate and in a microchannel formed in a substrate; and
   (b) arranging the cover plate over the substrate such that the cover plate in combination with the microchannel at least partially defines a conduit having a surface extending from an upstream region toward a downstream region and terminates at an opening, and the material deposited in step (a) forms an annular lining that conforms to the conduit surface at the downstream region and extends from the opening toward the upstream region in the conduit.

22. The method of claim 21, wherein step (a) is carried out through a vapor phase deposition technique.

23. The method of claim 22, wherein the vapor phase deposition technique is selected from the group consisting of evaporation and sputtering.

24. The method of claim 21, further comprising, after step (b), (c) depositing an emitter material on the annular lining, thereby producing an integrated emitter in situ.

25. The method of claim 24, wherein step (c) is carried out through electrodeposition of the emitter material onto the annular lining.

26. The method of claim 25, wherein the emitter material is electroplated onto the annular lining.

27. The method of claim 24, wherein step (c) is carried out through electroless deposition of the emitter material onto the annular lining.

28. A method for producing a microdevice, comprising:
   (a) providing a microdevice comprised of
      a substrate having a microchannel formed thereon,
      a cover plate arranged over the substrate such that the cover plate in combination with the microchannel at least partially defines a conduit within the microdevice, wherein the conduit has a surface that extends from an upstream region toward a downstream region and terminates at an opening, and
      an integrated emitter that is located within the conduit and conforms to the conduit surface at the downstream region; and
   (b) removing material from the cover plate and/or substrate about the opening, thereby forming an exterior microdevice surface and exposing a downstream portion of the emitter that protrudes from the exterior surface.

29. The method of claim 28, wherein step (b) is carried out through laser ablation.

30. The method of claim 28, wherein step (b) is carried out through reactive ion etching.

31. The method of claim 28, wherein step (b) is carried out through wet or dry chemical etching.

32. The method of claim 28, wherein step (b) is carried out through application of heat.

* * * * *